United States Patent [19]

Reif et al.

[11] Patent Number: 4,531,486
[45] Date of Patent: Jul. 30, 1985

[54] APPARATUS AND METHOD FOR MEASURING THE CONCENTRATION OF PARTICLES IN A GAS

[75] Inventors: Robert B. Reif, Grove City; Loren R. Albrechtson, Gahanna, both of Ohio

[73] Assignee: Battelle Development Corporation, Columbus, Ohio

[21] Appl. No.: 490,534

[22] Filed: May 2, 1983

[51] Int. Cl.$^3$ ............................................. G01N 15/00
[52] U.S. Cl. ............................... 123/198 DC; 73/28; 60/39.091; 123/198 D; 340/627
[58] Field of Search ................ 73/28, 432 PS, 861.09; 324/71.4, 454, 464; 340/627; 60/39.091, 39.092; 55/103, 104, 105, 140, 146, 150, 155, 270; 123/198 D, 198 DC

[56] References Cited

U.S. PATENT DOCUMENTS 2,491,445 12/1949 Cunningham et al. .......... 73/861.09
3,503,704 3/1970 Marks ..................................... 55/155
3,775,763 11/1973 Couch et al. ........................ 340/627

Primary Examiner—Stephen A. Kreitman
Attorney, Agent, or Firm—Sidney W. Millard

[57] ABSTRACT

The invention provides an apparatus and method for measuring the concentration of particles in a gas using an electrode disposed within but electrically insulated from an electrically-conductive conduit member, a current measuring device and means for maintaining the conduit member and the electrode at substantially the same potential. Flow of gas containing charged particles along the conduit induces a current passing from the electrode through the current measuring device. If the concentration of particles in the gas becomes excessive, the current measuring device activates a warning device or takes other action to prevent damage to any gas-consuming device attached to the apparatus. The apparatus might include an optional ionizer upstream of the electrode to charge the particles in the gas.

10 Claims, 6 Drawing Figures

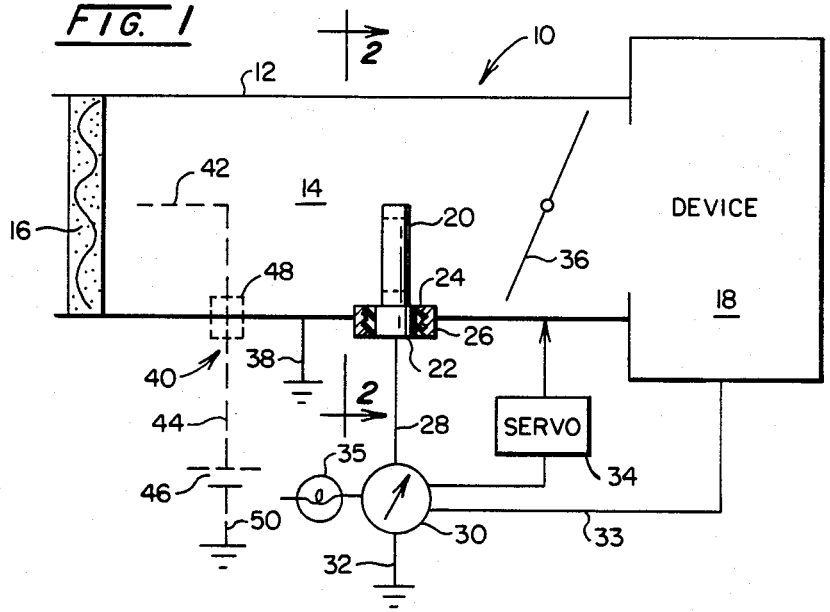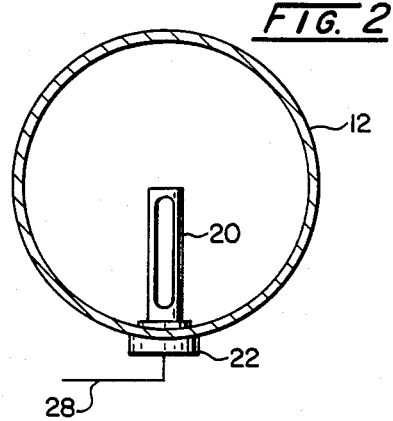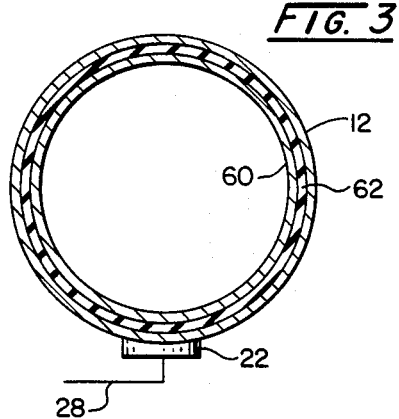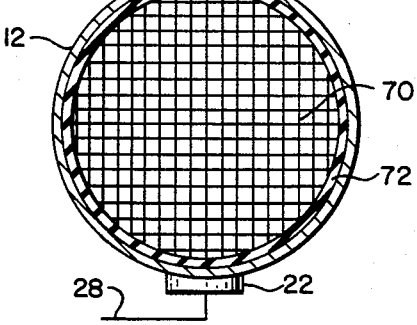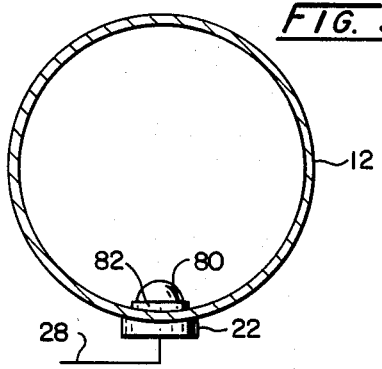

APPARATUS AND METHOD FOR MEASURING THE CONCENTRATION OF PARTICLES IN A GAS

BACKGROUND OF THE INVENTION

This invention relates to an apparatus and method for measuring the concentration of particles in a gas. Such particles may comprise, for example, dust, soot, smoke, solid pollutants and the like. The apparatus and method of the invention are especially intended for protecting engines and other gas receiving devices from damage caused by the intake of air containing too much dust or other particulate matter. However, the instant apparatus and method have a variety of other applications; for example, they may be used for checking the efficiency of dust removal equipment used in certain environmental control systems (e.g. removal of fibers from the air in textile mills, or dust in grain elevators) or for monitoring environmental pollution by checking the levels of particulate materials in waste gases such as flue gases, automobile exhaust systems, cement kilns and power generation plants.

Internal combustion engines used to power tanks and other military and other vehicles require a large supply of clean air to ensure maximum engine performance and engine life and to reduce maintenance requirements. Air cleaning systems have been developed that will remove 99% of the particulate matter that is drawn into the air intake system. Such high efficiency air cleaning systems are multi-stage units which include barrier type air filters. However, a simple dust leak in the air cleaning system (caused by, for example, accidental perforation of one of the air filters) can negate the effectiveness of the system. The vehicle operator must know when such a leak occurs so that he can shut off the engine and take steps to correct the problem before irreparable damage is done. This problem is especially of concern on military tanks equipped with gas turbine engines that are highly susceptible to damage by dust in the air under some operating conditions. Also, problems with excessively dusty air may be encountered in other internal combustion engines equipped with turbochargers. A reliable dust detection system can also be valuable on any engine and on many other systems where filters are used to remove dust from the air, either to provide a supply of clean air for a particular device or area or to control dust emission from a manufacturing operation or power generation system.

One prior art apparatus for measuring the concentration of particles in a gas is described in our U.S. Pat. No. 4,312,180 issued Jan. 26, 1982. This prior art apparatus passes particulate-carrying gas past first and second electrically conductive members spaced apart in a first region so as to provide a potential gradient in part of the region between the first and second members of at least about 30 kilovolts per centimeter. The first and second members thus form a corona and produce ions that charge a substantial proportion of the particles in the gas. Third and fourth electrically conductive members are spaced apart in a second region downstream from the first region and an electrical potential is applied between the third and fourth members so as to provide a potential gradient of substantially less than 30 kilovolts per centimeter therebetween. The charged particles produced in the first region are attracted to either the third or fourth electrically conductive member and there release their charge so that the current flowing from the third and fourth conductive members measures the concentration of particulate matter in the gas. Although this apparatus performs quite well, it does require the provision of two separate voltage sources. In addition, the apparatus cannot easily be retrofitted to existing pipework or similar ducts.

Another prior art apparatus for measuring the concentration of particles in a gas is described in U.S. Pat. No. 3,679,973 issued July 25, 1972 to N. S. Smith et al. In this prior art apparatus, the particulate-carrying gas is passed through a narrow throat, within which is located an ionizer which serves to charge the particles in the gas in substantially the same way as the first and second electrically conductive members in our own prior art apparatus described above. The air carrying the particles thus charged emerges from the throat into a wider duct, thereby reducing the rate of flow of the gas along the duct. The walls of wide duct are formed of a plurality of cylindrical, electrically-conductive members insulated from one another and each connected to a separate current measuring device. The reduction in flow velocity along the duct permits the particles to move radially of the duct onto the electrically-conductive members forming the walls of the duct, where they give up their charge to the electrically-conductive members, thereby causing a current flow through each measuring device. By measuring the current flow through the various current measuring devices, the concentration and size of the particles in the gas flow can be measured. This prior art apparatus is complicated; the specific apparatus shown in the drawings of the patent requires four separate electrically-conductive members with associated insulators therebetween, four current measuring devices and the voltage source necessary to charge the particles in the throat.

This invention seeks to provide an apparatus and method for measuring the concentration of particles in a gas which overcomes the aforementioned disadvantages of prior art apparatus and methods for this purpose. The invention also seeks to provide a method for retrofitting an apparatus for measuring the concentration of particles in a gas into an existing duct or similar structure.

SUMMARY OF THE INVENTION

This invention provides apparatus for measuring the concentration of particles in a gas comprising a conduit member formed of electrically-conductive material and having walls defining a conduit through which the gas can flow, an electrode at least part of which is disposed within the conduit and an insulator disposed between the conduit member and the electrode, thereby electrically insulating the electrode from the conduit member. The instant apparatus further comprises current measuring means or pulse counting means electrically connected to the electrode and potential maintaining means for maintaining the conduit member and the electrode at substantially the same potential.

The invention also provides a method for measuring the concentration of particles in a gas comprising providing a conduit member formed of electrically-conductive material and having walls defining a conduit, an electrode at least part of which is disposed within the conduit, an insulator disposed between the conduit member and the electrode from the conduit member, and current measuring means or pulse counting means electrically connected to the electrode. In the instant method, the conduit member and the electrode are maintained at substantially the same potential and the gas is passed through the conduit while at least some of the particles in the gas are electrically charged, thereby inducing a current flow through the current measuring means.

Finally, the invention provides a method of installing, in a conduit member formed of electrically-conductive material and having a wall defining a conduit passing therethrough, an apparatus for measuring the concentration of particles in gas passing through this conduit; this method comprises forming an aperture in the wall of the conduit member, passing through this aperture at least a part of an electrode, thereby disposing at least part of the electrode within the conduit, installing an insulator in the aperture and thereby electrically insulating the electrode from the conduit member, the electrode and the insulator together substantially sealing the aperture so as to prevent substantial gas leakage therethrough, and electrically connecting a current measuring means or pulse counting means to the electrode.

BRIEF DESCRIPTION OF THE DRAWINGS

FIG. 1 is a section through an apparatus of the invention, together with an associated gas filter and gas receiving device, the figure being largely schematic;

FIG. 2 is a section along the lines 2—2 in FIG. 1;

FIGS. 3-5 are sections similar to FIG. 2 but showing various other types of electrode which may be used in the instant apparatus.

DETAILED DESCRIPTION OF THE INVENTION

Figure 6:
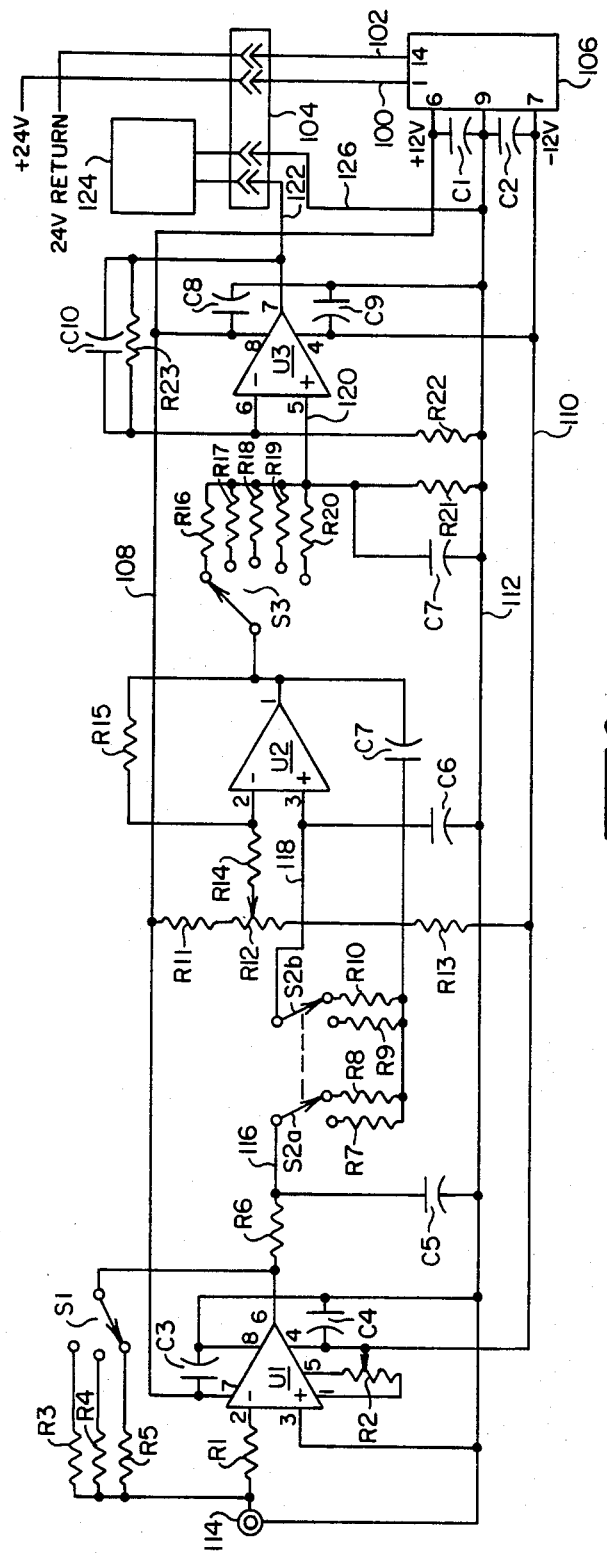
FIG. 6 is a partial circuit diagram of the current measuring device shown in FIG. 1.

As already mentioned, the instant apparatus comprises a conduit member, an electrode at least partially disposed within the conduit of the conduit member but insulated from the conduit member, a current measuring means or a pulse counting means connected to the electrode and a potential maintaining means for maintaining the conduit member and the electrode at substantially the same potential. Although the two variants of the invention using current measuring means and pulse counting means respectively are very similar in construction, their respective modes of operation are somewhat different and they will therefore be discussed separately below. The form of the instant apparatus using a pulse detecting means (hereinafter referred to as the "instant pulse counting apparatus") does not rely upon the particles actually contacting its electrode and giving up their charge to the electrode, unlike the prior art apparatus mentioned above; instead, in the instant pulse counting apparatus charged particles approaching the electrode induce a charge on the electrode which can be measured by a sensitive electrometer. As the charged particle passes the electrode, the induced charge on the electrode will be approximately equal to the charge on the particle and the induced current in the electrometer will drop to zero. Finally, once the charged particle has passed the electrode, the induced charge on the electrode begins to diminish and eventually drops to zero, thereby producing a current through the electrometer in the opposite direction to the current produced as the particle approaches the electrode. Thus, each separate charged particle or group of charged particles produce two pulses of opposite polarity as they pass the electrode, and these pulses can be measured by a conventional electronic pulse measuring circuit to indicate the concentration of dust in the gas stream.

However, one potentially serious disadvantage of the instant pulse counting apparatus is that a cloud of dust bearing substantially uniform charges will produce only a single pulse as the leading edge of the cloud first approaches the electrode and a single pulse as the trailing edge of the dust cloud leaves the electrode. Thus, to accurately measure the concentration of dust particles in a gas stream containing many such particles, the pulse counting means may be required to be of a relatively complicated type which can take account not only of the number of pulses generated but also of the interval between the two spaced pulses of opposite polarity produced by a dust cloud, with some form of integration device to calculate the total number of dust particles passing the electrode in such a cloud. Fortunately, if the instant pulse counting apparatus is only to be used to detect failure of a filter arrangement in a vehicle air intake system, such refinements may be unnecessary; dust clouds of uniform charge concentration are comparatively rare, the charge concentrations within such a dust cloud tending to vary and thus produce many pulses, so that if the apparatus is only to be used on a "yes/no basis" to detect failures in the air filtration system of a vehicle, relatively simple pulse detecting means should normally yield sufficiently good information. Furthermore, as described in more detail below, the performance of the instant pulse counting apparatus can be improved by using it in conjunction with a pulsed ionizer.

During work with the instant pulse counting apparatus, it was discovered that the baseline output of the electrometer circuit used for detecting the pulses steadily drifted in the same direction as the charge on the particles. When the electrometer circuit was modified so as to filter out the relatively high frequency pulses (thereby effectively converting the electrometer circuit to a current measuring circuit), it was found that the current measuring circuit showed a steady current dependent upon the particle concentration in the gas stream. It appears that, although the instant apparatus does not employ any strong electric field such as that employed in our aforementioned earlier U.S. Pat. No. 4,312,180 to force particles into contact with the detecting electrode, the space charge field produced by the charged particles passing along the conduit is sufficient to force the charged particles toward the walls of the conduit and to deposit them upon the electrode. This form of the apparatus of the invention, which employs a pulse measuring means rather than a pulse counting means, will hereinafter be referred to as the "instant current measuring apparatus" and is presently the preferred form of this invention.

Obviously, in the instant apparatus for a current flow or pulses to occur when the apparatus is in operation there will be a slight potential difference between the electrode and the conduit member, but in order for the current measuring means or pulse counting means to measure the small induced current, the potential maintaining means must maintain the conduit member and the electrode at substantially the same potential; this is of course in marked contrast to the apparatus described in our aforementioned earlier U.S. Pat. No. 4,312,180 in which (even in those cases where the conduit wall does function as one of the third and fourth electrically-conductive members) there is a very substantial potential difference between the electrode within the conduit and the conduit member itself. It most cases, it will be convenient to have as the potential maintaining means of the apparatus a connection between the conduit member and ground and a connection between the current measuring means and ground such that current from the electrode will flow through the current measuring means to ground. In referring to these "ground" connections, we are using the term "ground" in the broad sense in which it is normally used by those skilled in the art; for example, when the instant apparatus is installed on a vehicle, the ground connections will be made to the metal body of the vehicle, even though that body may not be at absolute ground potential.

In the instant apparatus, it is preferred that the electrode not offer serious resistance to gas flow along the conduit since an increase in gas flow resistance may affect the performance of any gas-receiving device connected to the conduit, especially where the instant apparatus is retro-fitted into an existing air intake for a gas receiving device, e.g. an internal combustion engine with a specifically designed air intake system. The presently preferred form of electrode for use in the instant apparatus comprises an elongate rod extending partway across the conduit in a direction substantially perpendicular to the flow of gas along the conduit; more particularly, the presently preferred form of electrode has the cylindrical rod having its axis substantially perpendicular to the flow of gas along the conduit, this cylinder having an aperture passing therethrough in a direction substantially perpendicular to the flow of gas. We have found that an electrode of this form has good sensitivity (i.e. it produces a relatively large induced current for a given flow of particles along the conduit) without offering substantial obstruction to gas flow. In addition, such a rod-shaped electrode is suitable for retro-fitting into an existing duct or pipe, as described in more detail below.

In saying that the conduit member of the instant apparatus must be formed of electrically-conductive material, we do not intend to restrict ourselves to conduit members formed of materials, such as copper and aluminum, which have sufficiently good conduction to function as the conductors in conventional electric circuits. It is only necessary that the conduit member be sufficiently conductive to prevent buildup of static charge thereon. Since buildup of static charge upon the conduit member will cause electrical effects which will seriously interfere with the measurement of, if not completely swamp, the small currents which must be measured by the current measuring means or pulse counting means of the instant apparatus. Thus, certain materials, such as some metal alloys, whose electrical resistance is considerably too large to be useful as conductors in conventional electrical circuits will have sufficient conductivity to be used in conduit members of the instant apparatus.

The currents which must be measured by the current measuring means of the instant apparatus are small; for example, we have found that when the particle-containing gas flowing through the instant apparatus is air containing about 10 mg. m$^{-3}$ of typical outdoor dust particles, the current through the current measuring means will normally lie in the range of $10^{-12}$–$10^{-13}$ amp. As those skilled in the art are aware, current measuring devices capable of measuring such small currents are now commercially available and such devices are sufficiently robust to make them suitable for insulation in environments, such as motor vehicles, where they are likely to be subjected to considerable vibration.

Since the instant apparatus depends for its operation upon the flow of charged particles along the conduit, obviously at least some of the particles in the gas flow along the conduit must carry charges. We have found that, in many of the environments in which the instant apparatus is to be employed, the particles in the gas will already bear charges which are sufficient to allow the instant apparatus to function properly. However, where the particles in the gas are not naturally charged, the instant apparatus may incorporate an ionizer disposed in the conduit such that the gas flow will pass the ionizer before it passes the electrode of the instant apparatus. Such an ionizer may be of any conventional type that will produce charging of the particles in the gas flow under the conditions encountered in practice. Where the instant apparatus employs a pulse counting means, it may be desirable to pulse the ionizer, thereby preventing the formation of uniform-charged clouds of dust which will only produce the same number of pulses as a single charged particle. Where the apparatus of the invention employs a current measuring means it will of course be undesirable to pulse the ionizer, and a steady ionizer voltage should be used instead.

As already mentioned, the instant apparatus may be used in an air filtering system to check that the filtering system is performing properly. Thus, the instant apparatus may include a filter for removing particles from the gas flow before the gas flow passes its electrode. The instant apparatus may also comprise a gas receiving device which receives the gas flow after the gas flow has passed the electrode and current response means for preventing damage to the gas receiving device whenever the current or pulse rate measured by the current measuring means or pulse counting means exceeds a predetermined value. Such a current response means may typically take the form of a servo mechanism responsive to the current measuring means and arranged to take action to prevent damage to the gas receiving device whenever the current indicating means indicates the presence of a predetermined concentration of particles in the gas flow past the electrode. For example, when the gas receiving device is an engine, the current response means may typically comprise a valve for blocking the flow of gas from the electrode to the engine and may also include means for stopping the engine, e.g. by interrupting the high tension current in the case of an engine relying upon spark ignition, or by interrupting the fuel supply in the case of a diesel engine. It is desirable that the current response means also include means for providing a warning signal such as a visible or audible alarm; when the instant apparatus is being used in a vehicle, it is of course desirable that a visible alarm be placed on the dashboard adjacent the normal instruments so that it will readily be visible to the driver.

Where the instant apparatus is employed in an air intake system with a filter or other dust-removing device which is subject to failure, upon failure of the filter the gas containing a very large concentration of particles may pass the electrode, with the risk that substantial quantities of particles may be deposited upon the electrode. Although the quantity of dust particles deposited upon the electrode after a single filter failure is not likely to greatly affect the operation of the electrode, after repeated filter failure, a sufficiently large quantity of dust particles may be deposited upon the electrode to reduce the sensitivity and/or reproducibility of operation of the apparatus. Accordingly, it is recommended that after each filter failure the electrode be inspected and, if necessary, cleaned to insure proper operation of the instant apparatus.

In saying that, in the instant installation method, the electrode and the insulator together substantially seal the aperture in the conduit member, we do not mean to imply that both the electrode and the insulator must perform this sealing function. For example, in certain embodiments of the invention, the electrode may lie wholly within the conduit and the sealing of the aperture be accomplished solely by the insulator, only a thin conductor passing from the electrode to the current measuring means through the insulator and thus through the aperture in the conduit member. In other embodiments of the invention, the electrode may lie partially within and partially outside the conduit member, the insulator having the form of a sleeve surrounding the electrode at the point where it passes through the wall of the conduit member, so that both the electrode and the insulator will be responsible for sealing the aperture.

The first embodiment of the invention shown schematically in FIGS. 1 and 2 of the accompanying drawings is a vehicle air intake system. The apparatus (generally designated 10) comprises a cylindrical conduit member or pipe 12 formed of steel and having a cylindrical conduit 14 through which air flows from an air filter 16 to a gas receiving device, which in this case has the form of an engine 18. The apparatus 10 further comprises an electrode 20 disposed within the conduit 14; this electrode 20 has the form of an elongate, cylindrical rod approximately equal in length to the radius of the cylindrical conduit 14 and extends radially of this conduit (i.e. perpendicular to the gas flow along the conduit 14) so that the free end of the electrode 20 lies approximately on the axis of the conduit 14.

The electrode 20 is mounted in an aperture in the wall of the pipe 12 by means of a cylindrical insulator 22, which serves to electrically insulate the electrode 20 from the metal wall of the pipe 12. The cylindrical wall of the insulator 22 is fixedly attached to a cylindrical metal sleeve 24, which surrounds the insulator 22 and which bears an external screw thread. This external screw thread engages a corresponding internal screw thread within a cylindrical sleeve 26 welded to and extending radially of the pipe 12. The screw thread engagement between the two sleeves 24 and 26 permits the electrode 20 to be readily removed from the pipe 12 when this is desirable for cleaning or replacement of the electrode 20.

A wire 28 extends from the electrode 20 through the insulator 22 to a current measuring device 30 located outside the pipe 12; the side of the current measuring device remote from the electrode 20 is grounded by a line 32. (Alternatively, the current measuring device 30 may be replaced by a pulse counting device.) The current measuring device 30 controls a current response means in the form of a servo mechanism 34 which is arranged to close a butterfly valve 36 dispersed within the conduit 14 between the electrode 20 and the engine 18 when the current through the current measuring device 30 exceeds a predetermined value. The current measuring device is also connected to a line 33, which can be used to shut down the engine 18, e.g. by interrupting an ignition circuit therein, and to a warning lamp 35 disposed on the dashboard of the vehicle on which the apparatus is mounted. The pipe 12 itself is grounded by a line 38.

If the apparatus 10 is to be used in environments in which the particles entrapped within the air stream flowing along the conduit 14 are not naturally charged to a degree sufficient to ensure proper operation of the apparatus, the apparatus 10 may optionally include an ionizer assembly, generally designated 40 and shown in broken lines in FIG. 1. This ionizer assembly may be of any conventional type; that shown in FIG. 1 comprises a pointed needle member 42 disposed at or along the axis of the conduit 14 and connected by a line 44 to one terminal of a high voltage source 46. (Those skilled in the art will be aware of various alternative forms of ionizer member which can be used in place of the needle member 42.) The line 44 is insulated from the pipe 12 by means of an insulator 48, while the other terminal of the high voltage source 46 is grounded by a line 50. (If the current measuring device 30 is replaced by a pulse counting device, the ionizer assembly should desirably include a pulsing device for pulsing the potential applied to the member 42.)

The apparatus 10 operates as follows. When the engine 18 is operating, air is drawn through the filter 16 and along the conduit 14. (If the optional ionizer assembly is in use, this ionizer assembly will charge particles in the air stream passing along the conduit 14; however, in the circumstances encountered in practice, the particles in the air stream may already bear sufficient charges and operation of the optional ionizer assembly 40 is not required.) The flow of the air containing the charged particles along the conduit 14 creates a flow of space charge within this circuit and this space charge deposits charged particles on the electrode 20 thereby causing a current flow from the electrode 20 through the current measuring device 30 and the line 32 to ground. While the filter 16 is operating normally, the current passing through the current measuring device 30 will remain below the predetermined level and the valve 36 will remain in the open position shown in FIG. 1 so that air flow to the engine 18 is not interrupted. If, however, for any reason (e.g. perforation of the filter 16) the concentration of particles in the air flow along the conduit 14 becomes too great, the current passing through the current measuring device 30 will exceed the predetermined value. When the current measuring device 30 registers this excessive current, it sends a signal to the servo mechanism 34, which closes the valve 36, thus cutting off the flow of dirty air to the engine 18 before the engine can become damaged. In addition, the current measuring device 30 sends a signal along the line 33 to shut down the engine in any appropriate manner, e.g. by cutting off the high tension supply to the ignition system of the engine or by interrupting the fuel supply on a diesel engine. Finally, the current measuring device 30 causes a current flow through the lamp 35, thus illuminating the warning lamp and advising the driver of the vehicle that the filter 16 has failed.

It will be appreciated that, when the instant apparatus is being used in certain types of vehicles (for example, highway trucks), the sudden shutdown of the engine 18 just described could be dangerous. Accordingly, when the engine 18 is of a type which can tolerate a short period of operation on dusty air without significant damage, it may be desirable to use a form of current measuring device 30 which gives an instant warning of failure of the filter 16, but which does not interrupt the air flow to the engine for a limited period (for example, 30 seconds), thus giving the driver a period in which to stop the vehicle without the engine being shut down.

The exact form of the electrode 20 is best seen in FIG. 2. As shown in that Figure, the electrode 20 has the form of an elongate cylindrical rod with a substantially rectangular cut-out extending radially therethrough in a direction parallel to the air flow along the conduit 14. We have found that this form of electrode gives good sensitivity without offering substantial resistance to air flow along the conduit 14, thus ensuring that the electrode 20 does not seriously interfere with air flow to the engine 18.

In addition, the form of the electrode 20 means that only a small aperture has to be cut in the wall of the pipe 12 in order to install the electrode in the pipe. In theory, this might suggest that an existing vehicle's system could be retro-fitted with an apparatus of the invention merely by cutting the small aperture necessary for insertion of the electrode 20 into some part of the existing air intake system without dismantling that system. However, we specifically do not recommend attempting to install an electrode in an existing air intake system without dismantling the system since there is a very grave risk that cutting the necessary aperture in the system will leave small metal particles within the system, and such small metal particles may eventually be swept by the air flow through the system into the engine or other gas-consuming device, with potentially disastrous results. Accordingly, if the instant apparatus is to be retrofitted into an existing air intake system, we recommend that the component of the system in which the electrode is to be installed be removed from the system before cutting the necessary aperture therein. Care should be taken to remove any metal or other filings resulting from the cutting of the aperture before the component is reassembled into the air intake system. However, the form of the electrode 20 may be useful where it is desired to offer the instant apparatus as an optional extra on, for example, a motor vehicle. The air intake system can be produced with the appropriate small aperture (and, if desired, with the sleeve 26 already fixed in the appropriate part of the air intake system). Thereinafter, the vehicles may be supplied with the apparatus already installed, or simply with a plug closing the appropriate aperture, this plug being readily removable if it is desired to retrofit the vehicle with an electrode.

FIGS. 3-5 illustrate other forms of electrodes which may be substituted for the electrode 20 shown in FIGS. 1 and 2. The electrode 60 shown in FIG. 3 has the form of a thin-walled hollow copper cylinder 60 co-axial with the pipe 12 and insulated therefrom by a thin-walled cylindrical insulator 62 which surrounds the copper cylinder 60. This type of electrode also gives good sensitivity and offers little resistance to air flow along the pipe 12.

The electrode 70 shown in FIG. 4 has the form of a copper grid extending across the whole of the conduit 14 and insulated from the wall of the pipe 12 by an insulating ring 72 in which the ends of the wires forming the grid 70 are embedded. This form of electrode also has good sensitivity but offers more resistance to air flow along the conduit than do the electrodes 20 and 60 previously described.

Finally, the electrode 80 shown in FIG. 5 has the form of a metal "button" or "mushroom" lying adjacent the wall of the pipe 12 and insulated therefrom by a flat, plate-like insulator 82. This form of electrode obviously offers little resistance to air flow along the conduit 14 and is suitable for retro-fitting in an existing pipe or duct, but has lower sensitivity than the electrode 20 shown in FIGS. 1 and 2. The sensitivity of the electrode 80 may be improved by elongating the electrode parallel to the axis of the pipe 12 (so that the electrode 80 has substantially the form of a hemi-cylinder having its axis parallel to the axis of the pipe 12).

FIG. 6 shows a partial circuit diagram of the current measuring device 30 shown in FIG. 1. FIG. 6 shows the amplifying part of the current measuring device connected to a bar graph light emitting diode (LED) array which provides a visual indication of the current passing through the current measuring device and which can, if desired, be provided instead of or in addition to the warning lamp 35. The switching circuits necessary to activate the servo mechanism 34, the warning lamp 35, and the engine control line 33 are not shown in FIG. 6 since they are entirely conventional and appropriate circuits will readily be apparent to those skilled in the art.

The circuit shown in FIG. 6 is powered from a 24 V D.C. supply applied between a positive supply line 100 and a return line 102. The lines 100 and 102 are connected, via a four-pin connector 104, to pins 1 and 14 respectively of a voltage stabilization circuit 106, which is an Integrated Circuits DIP 24 1212DB integrated circuit. This integrated circuit produces a +12 V output on its pin 6 which is connected to a positive supply line 108, a −12 V output on its pin 7 which is connected to a negative supply line 110, and a common or ground output at its pin 9 which is connected to a ground line 112. A smoothing capacitor C1 is connected between the positive supply line 108 and the ground line 112, while a second smoothing capacitor C2 is similarly connected to the negative supply line 110 and the ground line 112.

The input to the current measuring device from line 28 (FIG. 1) is received at a socket 114, one terminal of this socket being connected to the ground line 112 and the other terminal of the socket being connected via a resistor R1 to the negative input (pin 2) of an integrated circuit U1. (To provide the necessary input impedance, resistor R1 preferably has a value of the order of $10^{10}$ ohms.) This integrated circuit U1 is an Intersil ICH 8500 ACTV amplifier circuit, which is an electrometer amplifier circuit having a very high input impedance. The positive input (pin 3) of integrated circuit U1 and pin 8 thereof are connected directly to the ground line 112, pin 4 is connected directly to the negative supply line 110, and pin 7 directly to the positive supply line 108. A capacitor C3 is connected between pins 7 and 8 (thus bridging the positive supply and ground lines 108 and 112 respectively) while a further capacitor C4 is connected between pins 4 and 8, thus bridging the negative supply and the ground lines 110 and 112 respectively. Finally, pins 1 and 5 of integrated circuit U1 are bridged by resistance R2, which forms a part of a potentiometer, the movable terminal of this potentiometer being connected to the negative supply line 110.

The output from integrated circuit U1 appears at pin 6. A variable feedback loop is provided for integrated circuit U1, the output from pin 6 of U1 being supplied to a three-position switch S1 which can be used to place any one of three different resistors R3, R4 and R5 in series with resistor R1 between pins 6 and 2 of integrated circuit U1. By selecting different ones of the resistors R3, R4 and R5, the range of current measured by the circuit can be varied. The output from pin 6 of U1 is also supplied via a resistor R6 to a line 116 which is connected to the removable terminal of a two-position selector switch S2a. This switch can be used to place one of two resistors R7 and R8 in series with R6. The common output of R7 and R8 is connected to a common iput of two resistors R9 and R10, one of which can be selected by a switch S2b which is ganged with S2a so that either R7 and R9 or R8 and R10 can be placed in series with R6. The output from switch S2b is conveyed by a line 118 to the positive input (pin 3) of an integrated circuit U2. Capacitors C5 and C6 connect the ground line 112 to the lines 116 and 118 respectively; thus, C5 and C6 together with resistors R7/R8 and R9/R10 respectively, form two RC circuits which effect low-pass filtering of the output from U1 before it reaches U2.

The integrated circuit U2 actually comprises one-half of a Texas Instruments TLO 72 double linear amplifier integrated circuit, the other half of this double amplifier being the integrated circuit U3 described below. As is conventional, power supply connections to the double amplifier are only shown on one of the amplifier components, in this case U3. To provide a variable negative input for U2, resistors R11, R12 and R13 are arranged in series as a voltage divider between the positive and negative supply lines 108 and 110 respectively and an appropriate voltage, which can be varied by the operator, is tapped from R12 and fed via a resistor R14 to the negative input (pin 2) of U2. This tapping of the variable voltage from R12 enables the amplifier U2 to be adjusted for any offset on the incoming signal due to e.g. small leakage currents even when no dust is present in the air flowing along the conduit 14 (FIG. 1). The output of U2 appears at pin 1 thereof and, to establish appropriate feedback, this output is fed via a resistor R15 to pin 2 thereof and via a capacitor C7 to the common input of resistors R9 and R10. The output from pin 1 of U2 is also fed to the movable terminal of a five-position selector switch S3, which places one of five different resistors R16, R17, R18, R19 and R20 between the output of U2 and a line 120 connected to the positive input (pin 5) of the aforementioned integratec circuit amplifier U3. An RC circuit comprising a capacitor C7 in parallel with a resistor R21 is connected between the line 120 and the ground line 112. The negative input (pin 6) of U3 is connected via a resistor R22 to the ground line 112. The positive and negative power supply inputs, pins 8 and 4 respectively, of U3 are connected to the positive and negative supply lines 108 and 110 respectively; those pins 8 and 4 are also connected via capacitors C8 and C9 respectively to the ground line 112. The switch S3 and the associated resistors R16/R20 allow adjustment of the overall gain provided by the amplifiers U2 and U3.

The output from U3 appears at pin 7 thereof. To provide proper feedback, this output is fed back via an RC circuit comprising a capacitor C10 connected in parallel with a resistor R23 to the negative input (pin 6) of U3. The output from U3 is also fed via a signal line 122 and the 4-pin connector 104 to a bar graph LED array 124, which is of the commercially available National Semiconductor Model NSM 3914 type. A signal return line 126 from array 124 is connected by the 4-pin connector 104 to the ground line 112.

It will thus be seen that the circuit shown in FIG. 6 provides a three-stage amplification of the incoming signal from the socket 114, these three stages of amplification being effected by the integrated circuits U1, U2 and U3 respectively. The circuit provides for adjustment of range, offset, and gain by means of the switch S1, the variable voltage applied to the negative input of amplifier U2, and the switch S3 respectively and also provides for filtering of the incoming signals by the RC circuits formed by the capacitors C5 and C6 in association with the resistors R7/R8 and R9/R10 respectively. Thus, the circuit shown in FIG. 6 converts the very small currents, of the order of $10^{-12}$ to $10^{-13}$ amps. flowing through the resistor R1 and the socket 114 to a varying voltage on line 122 sufficient to drive the LED array 124.

The circuit shown in FIG. 6 is an experimental prototype and is deliberately provided with variable range, filter and gain settings in order to enable it to be used with a variety of types of apparatus of the invention. Those skilled in the art will appreciate that production models of such a circuit, intended only for use with one particular type of electrode in a specific vehicle or other environment, will not normally require such variability, thus permitting considerable simplification of the circuitry; in such an invariable production model, a single resistor could replace the resistors R3, R4 and R5 and the switch S1, a second single resistor could replace the switch S2 and the resistors R7, R8, R9 and R10, while a third single resistor could replace the switch S3 and the resistors R16–R20.

Although the circuit shown in FIG. 6 has been described above as a current measuring circuit, it can readily be modified to act as a pulse detecting circuit merely by changing the values of certain components. As will be appreciated from the description given above as to mode of operation of both the pulse counting and current measuring types of the instant apparatus, the current actually induced in a line connecting the electrode 20 (FIG. 1) to ground will be the same in both cases, the signal comprising a direct current caused by the deposition of charged particles on the electrode, but superimposed upon this direct current will be "spikes" or pulses produced by induction of the charges on the electrode as dust particles pass the electrode 20 without being deposited thereon. Thus, a current measuring circuit used in the instant apparatus should be equipped with a low-pass filter with a cut-off frequency sufficiently low to eliminate the pulses in the incoming signal; in practice, this cut-off frequency is preferably about 1 Hz. In the circuit shown in FIG. 6, a cut-off frequency of about 1 Hz. can be achieved by using resistors R8 and R10 of about 1 megaohm, giving C5 a value of 2.2 microfarad and capacitor C6 a value of 1 microfarad. In fact, the cut-off frequency of the circuit shown in FIG. 6 is in practice regulated not only by the RC circuits formed by the capacitors C5 and C6 together with the resistors R7–R10, but also by the input resistor R1. To provide a high input resistance to the circuit, we prefer to make the resistor R1 about $10^{10}$ ohms, and such a resistor will have an inherent capacity of about 10 picofarad. Thus, resistor R1 alone acts as a filtering RC circuit with a cut-off frequency of around 2 Hz.

Obviously, to modify the circuit shown in FIG. 6 so that it acts as a pulse counting circuit, it will be necessary to raise the cut-off frequency of the circuit. This may conveniently be done by reducing R1 to about $10^8$ ohms, and reducing resistors R8 and R10 to about 100 kiloohms, thereby raising the cut-off frequency to around 10 Hz. Those skilled in the art will also appreciate that it will be necessary to pass the output from the circuit shown in FIG. 6 to a conventional pulse counting device rather than to a bar graph array.

The apparatus of the invention is small, rugged, relatively insensitive to vibration and requires little or no power (even when the optional ionizer is employed, the power consumption will usually be lower than the prior art devices described above). The instant apparatus operates much faster than existing devices which collect a sample of the dust in a filter and measure the pressure drop across the filter. The instant apparatus will also be more sensitive than prior art devices which measure the effect of the dust upon a corona current and is more rugged that the light scattering type of particle monitors and densitometer-type smoke meters.

It will be apparent to those skilled in the art that numerous changes and modifications can be made in the preferred embodiments of the instant apparatus and method already described without departing from the scope of the invention. Accordingly, the foregoing description is to be construed in an illustrative and not in a limitative sense, the scope of the invention being defined solely by the appended claims.

We claim:

1. Apparatus for automatically stopping air flow to an engine when the air contains an unacceptable level of solid particles, said apparatus comprising, means for forming an air tight conduit having an axis, said conduit being in fluid communication with a source of air and leading to said engine, means for electrically grounding said conduit, means for pulling air from said source through said conduit to said engine, a filter in said conduit for collecting solid particles drawn into said conduit from said source, said filter being located in said conduit between said source and said engine and so mounted that all air flowing to said engine must flow through said filter, means within said conduit between the filter and the engine for imparting an electrical charge to solid particles in said conduit which have passed said filter, an electrode located in said conduit between said charge imparting means and said engine, said electrode being a hollow cylinder, said cylinder being oriented coaxially with said conduit, said electrode and conduit being configured to require all air reaching said engine to pass through the area circumscribed by said electrode, said electrode having the property of collecting at least some of the electrical charge imparted to said particles as said particles pass through the cylindrical electrode, means for draining the charge from said electrode and measuring the magnitude of electrical current flow in said draining means, means for stopping air flow in said conduit when the magnitude of said measured flow reaches a predetermined level.

2. The apparatus of claim 1 wherein said stopping means comprises a value within said counduit.

3. The apparatus of claim 2 wherein the valve is a butterfly valve located between the electrode and the engine.

4. The apparatus of claim 3 including a visual alarm signal associated with said measuring means.

5. The apparatus of claim 4 including means for stopping said engine when the magnitude of said measured flow reaches said predetermined level.

6. The apparatus of claim 3 including means for stopping said engine when the magnitude of said measured flow reaches said predetermined level.

7. The apparatus of claim 2 including means for stopping said engine when the magnitude of said measured flow reaches said predetermined level.

8. The apparatus of claim 2 including a visual alarm signal associated with said measuring means.

9. The apparatus of claim 1 including means for stopping said engine when the magnitude of said measured flow reaches said predetermined level.

10. The apparatus of claim 1 including a visual alarm signal associated with said measuring means.

* * * * *